(12) United States Patent
Anderson

(10) Patent No.: US 10,894,139 B2
(45) Date of Patent: Jan. 19, 2021

(54) OXYGEN TREATMENT DEVICE FOR MAMMALS

(71) Applicant: ERGO-FLEX TECHNOLOGIES, LLC, Conroe, TX (US)

(72) Inventor: J. T. Anderson, Conroe, TX (US)

(73) Assignee: Ergo-Flex Technologies, LLC, Conroe, TX (US)

( * ) Notice: Subject to any disclaimer, the term of this patent is extended or adjusted under 35 U.S.C. 154(b) by 182 days.

(21) Appl. No.: 15/914,888

(22) Filed: Mar. 7, 2018

(65) Prior Publication Data

US 2018/0193583 A1     Jul. 12, 2018

Related U.S. Application Data

(60) Provisional application No. 62/619,387, filed on Jan. 19, 2018.

(51) Int. Cl.
    *A61M 16/10*      (2006.01)
    *A61B 5/00*      (2006.01)
    (Continued)

(52) U.S. Cl.
CPC ......... *A61M 16/101* (2014.02); *A61B 5/0022* (2013.01); *A61M 16/12* (2013.01); *A63B 23/18* (2013.01); *A61B 5/021* (2013.01); *A61B 5/024* (2013.01); *A61B 5/0816* (2013.01); *A61B 5/1118* (2013.01); *A61B 5/14542* (2013.01);
(Continued)

(58) Field of Classification Search
CPC ....... A61B 5/021; A61B 5/02416; A61B 5/08; A61B 5/082; A61B 5/14551; A61B 5/14553; A61B 5/412; A61B 5/4818; A61B 5/4875; A61M 16/00; A61M 16/0045; A61M 16/024; A61M 16/026; A61M 16/0627; A61M 16/0672; A61M 16/10; A61M 16/101; A61M 16/107; A61M 16/1075; A61M 16/12; A61M 16/125; A61M 2016/0039; A61M 2016/0042; A61M 2016/1025; A61M 2202/0225; A61M 2205/3561; A61M 2205/6018; A61M 2230/005; A61M 2230/06; A61M 2230/202; A61M 2230/205; A61M 2230/30; A61M 2230/42; A61M 2230/435; A61M 2230/50; A61M 2230/60; B01D 2253/108; B01D 2253/25; B01D 2256/12; B01D 2257/102; B01D 2259/40007; B01D 2259/40009; B01D 2259/40052;
(Continued)

(56) References Cited

U.S. PATENT DOCUMENTS 4,889,116 A * 12/1989 Taube .................. A61M 16/00
                                               128/204.23
5,251,632 A * 10/1993 Delpy ................ A61B 5/14553
                                               128/204.23
(Continued)

*Primary Examiner* — Annette Dixon
(74) *Attorney, Agent, or Firm* — Tumey L.L.P.

(57) ABSTRACT

Method and apparatus varies the oxygen concentration level of air delivered to a person for treatment on training purposes. The apparatus includes a display device for displaying current physiological data as well as data from previous sessions for comparison purpose. The oxygen level is precisely controlled by a central processing unit in response to input data from the person.

3 Claims, 1 Drawing Sheet

(51) Int. Cl.
*A61M 16/12* (2006.01)
*A63B 23/18* (2006.01)
*A61M 16/00* (2006.01)
*A61M 16/06* (2006.01)
*A61B 5/08* (2006.01)
*A61B 5/11* (2006.01)
*A61B 5/145* (2006.01)
*A61B 5/024* (2006.01)
*A61B 5/021* (2006.01)

(52) U.S. Cl.
CPC ........... *A61B 5/4836* (2013.01); *A61B 5/4839* (2013.01); *A61B 5/4866* (2013.01); *A61B 2503/10* (2013.01); *A61B 2505/09* (2013.01); *A61M 16/024* (2017.08); *A61M 16/06* (2013.01); *A61M 2016/003* (2013.01); *A61M 2016/103* (2013.01); *A61M 2202/0208* (2013.01); *A61M 2205/52* (2013.01); *A61M 2230/06* (2013.01); *A61M 2230/30* (2013.01); *A61M 2230/50* (2013.01)

(58) Field of Classification Search
CPC ...... B01D 2259/402; B01D 2259/4533; B01D 53/047; B01D 53/053
See application file for complete search history.

(56) References Cited

U.S. PATENT DOCUMENTS

| | | | | |
|---|---|---|---|---|
| 5,682,877 | A * | 11/1997 | Mondry | A61M 16/10 128/204.22 |
| 5,906,672 | A * | 5/1999 | Michaels | B01D 53/047 95/12 |
| 2005/0113709 | A1* | 5/2005 | Millet | A61B 5/08 600/529 |
| 2008/0066752 | A1* | 3/2008 | Baker | A61M 16/026 128/204.23 |
| 2011/0077474 | A1* | 3/2011 | Huiku | A61B 5/02416 600/301 |

* cited by examiner

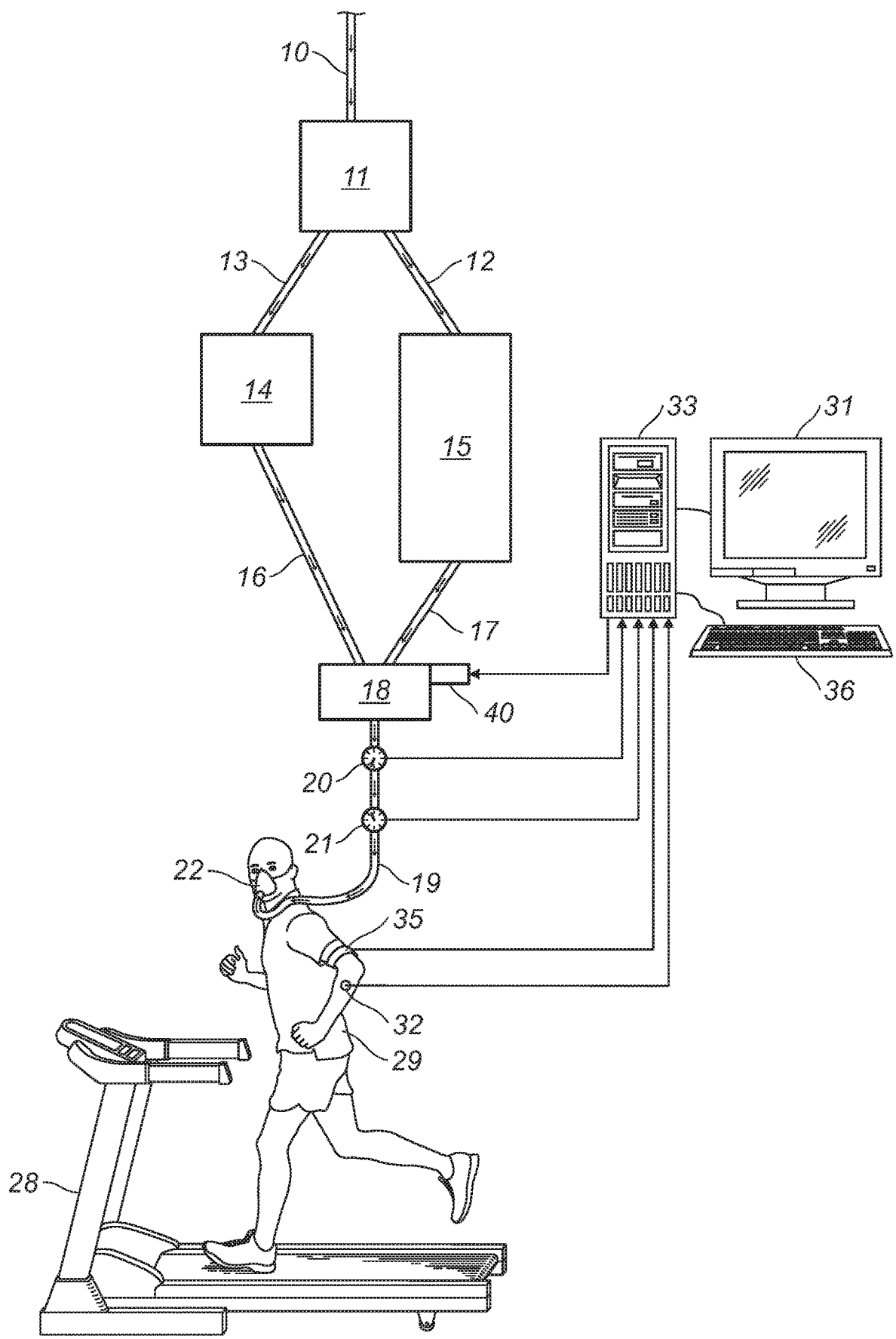

OXYGEN TREATMENT DEVICE FOR MAMMALS

This application claims priority to provisional application Ser. No. 62/619,387 filed Jan. 19, 2018, the entire content of which is incorporated herein by reference thereto.

BACKGROUND OF INVENTION

Field of the Invention

This invention is directed to a method and apparatus for regulating the concentration of oxygen in air delivered to a person for breathing. The apparatus and method can be used to improve the oxygen level in a person's blood and also to train an individual for athletic activities, (such as football, track and field) in geographical areas of higher elevation.

Description of Related Art

Systems for delivering varying concentrations of oxygen to people for training purposes are known. However they are not designed to provide precise concentrations of oxygen. Also they do not include sufficient monitoring or measuring devices for the physiological measurements so that instantaneous information (such as heat rate, blood oxygen level, blood pressure as well as data related to the improvement of blood oxygen levels and other data compared to previous exercising sessions) can be calculated and displayed on a monitor.

This invention is adapted to supply a precise concentration of oxygen in air to a person for training or health reasons. The system includes a plurality of monitors and sensors for measuring the physiological characteristics of a person while exercising and at the same time displaying the information and comparing it to a previous test.

BRIEF DESCRIPTION OF THE DRAWING

The FIGURE is a schematic drawing showing the components of an apparatus according to one embodiment of the invention.

DETAILED DESCRIPTION OF THE INVENTION

As shown in the FIGURE, ambient air enters an oxygen concentrator 11 via conduit 10. Concentrated oxygen enters a closed reservoir 15 via conduit 12 and the exhaust leaves concentrator 11 via conduit 13 to a closed reservoir 14. The exhaust air his a lower concentration of oxygen than that of the ambient air.

Reservoirs 14 and 15 are connected to a valve 18 via conduits 16 and 17. Valve 18 is controlled via an actuator 40 by a central processing unit 33 to control the oxygen level of the air leaving valve 18. The air is a mixture of concentrated oxygen and the exhaust produced from concentrator 11. The air is conveyed to a breathing mask 22 via a conduit 19. Flow meter 20 and an oxygen concentration meter 21 may be located within conduit 19. The patient or athlete 23 is thus supplied air the oxygen content of which may be varied.

The patient or athlete 29 is subjected to physical activity for example a treadmill 28. The subject's blood pressure, heart rate, blood oxygen level and other physical characteristics are measured by sensors 35, 32 for example and the data is sent to the central processing unit 33. The central processing unit processes the data and can vary the oxygen concentration of the air supplied to the subject by wireless manipulation of the valve 18 by actuator 40 according to algorithms stored in the CPU.

A display device 31 is connected to the CPU so that real time information is visible to the subject. This information can include the subject's blood pressure, heart rate, oxygen blood level, temperature etc. A keyboard 36 for data input is also provided.

Information such as the subject's sex, height, weight, age, medical history etc. can be inputted to the CPU.

One use of the apparatus can be to train athletes for competition at higher altitudes. Valve member 18 can be set to deliver an oxygen concentration of level about 21% which is normal. The subject will exercise to raise their heart beat rate to a target level. At that point the oxygen concentration of air is fed to the subject at the desired elevation which will be lower than 21% to simulate the less dense air at higher elevations. For example at 6000 ft the effective oxygen level is 16.6%. The effect of lowering the oxygen concentration on the subject's heartbeat, blood pressure and blood oxygen level can be monitored and stored in the CPU.

After a given period of time the oxygen concentration can be raised to 21% and the time it takes for the subject's heart rate to return to the baseline level can be measured as well as the oxygen blood level. Subsequent tests can be performed to measure the subject's improvement in recovery time and also in blood oxygen levels, as well as the subject's endurance. All this information can be displayed on display 31 in real time and can be compared to prior tests.

Another use is to supply air with increased oxygen levels to a patient in order to raise the oxygen levels in a patient's blood. Repeated treatments have resulted in removing toxins from the blood and increasing blood oxygen levels. These results can have a positive effect on the functioning of a person's organs and an overall improvement in a person's health.

Reservoirs 14 and 15 may be fabricated using gas impermeable fabric or cloth and may be separate from each other or attached at a common point.

Display 31 may include several screens so that different parameters may be displayed concurrently.

The sensors and flow meters may communicate with the CPU wirelessly and vice versa.

What is claimed is:

1. Apparatus for delivering a precise concentration of oxygen in air to a person comprising;
   a) an oxygen concentrator having an outlet for oxygen and an outlet for exhaust air;
   b) a mixing valve having an input for oxygen from the concentrator, an input for exhaust air from the concentrator, and an output for a mixture of exhaust air and oxygen from the concentrator,
   c) an air mask and air conduit connected to the mixing valve output,
   d) a flow meter and an oxygen concentration meter connected to the air conduit, and connected to a central processing unit,
   e) a plurality of physiological sensors connected to the central processing unit,
   f) a display device connected to the central processing unit,
   g) the central processing unit being programed to control the mixing valve in response to inputs from the flow meter, the oxygen concentration meter, and the plurality of physiological sensors.

2. Apparatus as claimed in claim 1 wherein the display device includes a plurality of screens.

3. Apparatus as claimed in claim 1 wherein the central processing unit is programed to store data from a first testing session and to compare current data with data from a previous session and to display the information on the display device.

\* \* \* \* \*